United States Patent [19]

Poss

[11] Patent Number: 5,191,086

[45] Date of Patent: Mar. 2, 1993

[54] IMIDAZOLE AND BENZIMIDAZOLE DERIVATIVES

[75] Inventor: Michael A. Poss, Lawrenceville, N.J.

[73] Assignee: E.R. Squibb & Sons, Inc., Princeton, N.J.

[21] Appl. No.: 671,328

[22] Filed: Mar. 19, 1991

[51] Int. Cl.$^5$ .............. C07D 403/10; C07D 233/60; C07D 233/54

[52] U.S. Cl. .................. 548/252; 548/343.1; 548/342.1; 548/253; 548/254; 548/329.1; 548/330.1; 548/340.1; 548/341.5; 548/342.5; 548/345.1; 548/346.1; 548/330.5; 548/327.1; 548/337.1; 548/335.5

[58] Field of Search ............... 548/252, 343, 338, 342, 548/253, 254

[56] References Cited

U.S. PATENT DOCUMENTS

| | | | |
|---|---|---|---|
| 4,207,324 | 6/1980 | Matsumura et al. | 514/397 |
| 4,340,598 | 7/1982 | Furukawa et al. | 514/400 |
| 4,355,040 | 10/1982 | Furukawa et al. | 514/400 |
| 4,582,847 | 4/1986 | Furukawa et al. | 514/400 |
| 4,812,462 | 3/1989 | Blankley et al. | 514/303 |
| 4,816,463 | 3/1989 | Blankley et al. | 514/293 |
| 4,820,843 | 4/1989 | Aldrich et al. | 424/480 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |

FOREIGN PATENT DOCUMENTS

| | | |
|---|---|---|
| 253310 | 1/1988 | European Pat. Off. . |
| 323841 | 7/1989 | European Pat. Off. . |
| 324377 | 7/1989 | European Pat. Off. . |

Primary Examiner—David B. Springer
Attorney, Agent, or Firm—Theodore R. Furman, Jr.

[57] ABSTRACT

Novel angiotensin-II receptor antagonists are disclosed having the general formula

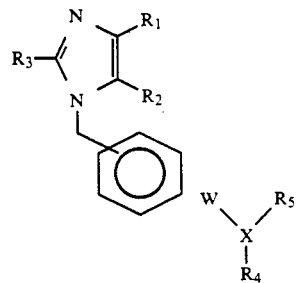

wherein $R_1$, $R_2$, $R_3$, $R_4$, $R_5$, W and X are as defined herein.

3 Claims, No Drawings

IMIDAZOLE AND BENZIMIDAZOLE DERIVATIVES

FIELD OF THE INVENTION

The present invention relates to novel substituted imidazoles which are useful as antihypertensive agents.

SUMMARY OF THE INVENTION

In accordance with the present invention, novel compounds which inhibit the action of the hormone angiotensin II are disclosed. These compounds are of the general formula

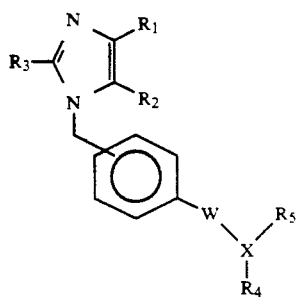

and pharmaceutically acceptable salts thereof;

W can be O, S, NH or $CH_2$;

if W=O, S or NH, then $X = CR_4'$;

if W=$CH_2$, then $X=CR_4'$ or N;

$R_1$ is independently selected from hydrogen, halogen, $-NO_2$, $-CF_3$ or $-CN$;

$R_2$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$-imidazol-1-yl; $-(CH_2)_m$-1,2,3-triazolyl optionally substituted with one or two groups selected from $CO_2R_7$ or alkyl of 1 to 4 carbon atoms; $-(CH_2)_m$-tetrazolyl; $-(CH_2)_nOR_6$;

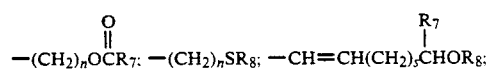

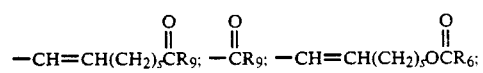

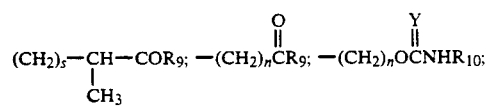

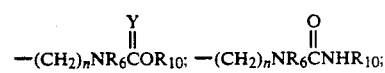

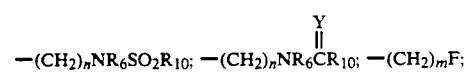

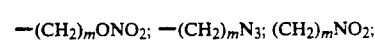

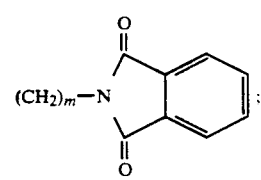

or $R_1$ and $R_2$ taken together with the carbon atoms of the imidazole nucleus to which they are attached can form a benzimidazole shown as

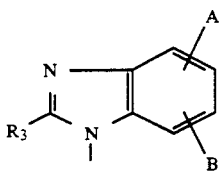

wherein

A can be hydrogen, alkyl, $C_xF_{2x+1}$, $C_6F_5$, halogen, $C_{1-6}$alkoxy, $-(CH_2)_xOH$, $-(CH_2)_x-OC_{1-4}$ alkyl,

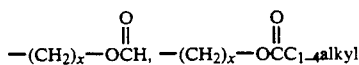

or $-COR_9$ and B can be hydrogen, alkyl, $C_xF_{2x+1}$, $C_6F_5$, halogen or $C_{1-6}$alkoxy;

$R_3$ is alkyl of 2 to 10 carbon atoms, alkenyl or alkynyl of 3 to 10 carbon atoms or the same groups substituted with F or $CO_2R_7$; cycloalkyl of 3 to 8 carbon atoms, cycloalkylalkyl of 4 to 10 carbon atoms; cycloalkylalkenyl or cycloalkylalkynyl of 5 to 10 carbon atoms; $(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) optionally substituted with F or $CO_2R_7$; benzyl or benzyl substituted on the phenyl ring with 1 or 2 halogens, alkoxy of 1 to 4 carbon atoms, alkyl of 1 to 4 carbon atoms or nitro;

$R_4$ and $R_4'$ are each independently hydrogen, alkyl of 1 to 10 carbon atoms, alkenyl or alkynyl of 3 to 10 carbon atoms, cycloalkyl of 3 to 8 carbon atoms, cycloalkylalkyl of 4 to 10 carbon atoms, cycloalkylalkenyl or cycloalkylalkynyl of 5 to 10 carbon atoms, aryl or aryl substituted with any $R_5$ group, benzyl or benzyl substituted on the phenyl ring with 1 or 2 halogens, alkoxy of 1 to 4 carbon atoms, alkyl of 1 to 4 carbon atoms, nitro, or any $R_5$ group;

If X=C, then $R_5$ is $-COOR_7, -NHSO_2CF_3$,

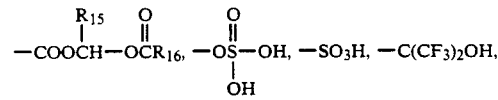

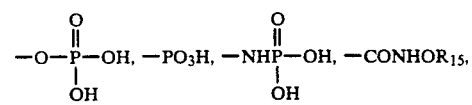

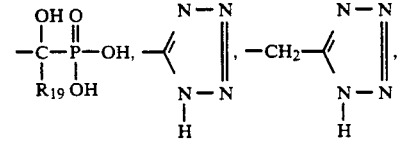

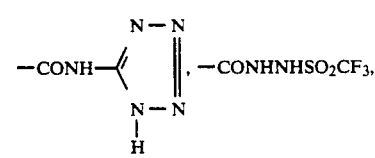

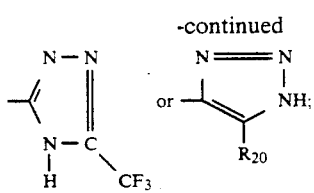

if X=N, then $R_5$ is —C(CF$_3$)$_2$OH, —CONHOR$_{15}$,

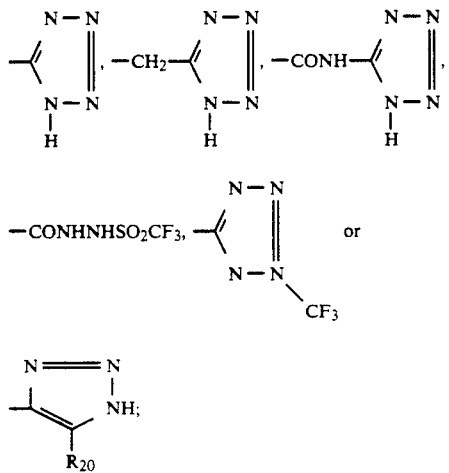

$R_6$ is H, alkyl of 1 to 6 carbon atoms, cycloakyl of 3 to 6 carbon atoms, phenyl or benzyl;

$R_7$ is H, alkyl or perfluoroalkyl of 1 to 8 carbon atoms, cycloalkyl of 3 to 6 carbon atoms, phenyl or benzyl;

$R_8$ is H, alkyl of 1 to 6 carbon atoms, cycloalkyl of 3 to 6 carbon atoms, phenyl, benzyl, acyl of 1 to 4 carbon atoms, phenacyl;

$R_9$ is H, alkyl of 1 to 6 carbon atoms, cycloalkyl of 3 to 6 carbon atoms, (CH$_2$)$_p$C$_6$H$_5$, OR$_{11}$ or NR$_{12}$R$_{13}$;

$R_{10}$ is alkyl of 1 to 6 carbon atoms or perfluoroalkyl of 1 to 6 carbon atoms, 1-adamantyl, 1-naphthyl, 1-(1-naphthyl)ethyl, or (CH$_2$)$_p$C$_6$H$_5$;

$R_{11}$ is H, alkyl of 1 to 6 carbon atoms, cycloalkyl of 3 to 6 carbon atoms, phenyl or benzyl;

$R_{12}$ and $R_{13}$ independently are H, alkyl of 1 to 4 carbon atoms, phenyl, benzyl, α-methylbenzyl, or taken together form a ring of the formula

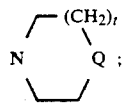

Q is NR$_{14}$, O or CH$_2$;

$R_{14}$ and $R_{15}$ are independently H, alkyl, aryl, aralkyl or cycloalkyl;

$R_{16}$ is C$_{1-6}$alkyl, —NR$_{17}$R$_{18}$ or

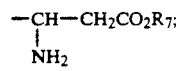

$R_{17}$ and $R_{18}$ are independently H, C$_{1-6}$alkyl, benzyl or taken together are 3 to 6 carbon atoms forming a 4- to 7-membered ring with the nitrogen atom to which they are attached;

$R_{19}$ is H, C$_{1-5}$alkyl, phenyl;

$R_{20}$ is —CN, —NO$_2$ or —CO$_2$R$_7$;

Y=O or S;
Z=O, NR$_6$ or S;
m is 1–5;
n is 1–10;
p is 0–3;
q is 2–3;
r is 0–2;
s is 0–5;
t is 0 or 1; and
x is 1 to 6.

DETAILED DESCRIPTION OF THE INVENTION

In its broadest aspects the present invention relates to the compounds of formula I and to pharmaceutical compositions and methods employing such compounds.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen", as used by itself or as part of a larger group refers to fluorine, chlorine, bromine and iodine with fluorine and chlorine being preferred.

To prepare the compounds of formula I where R$_1$ and R$_2$ do not form a benzene ring, a compound of the formula

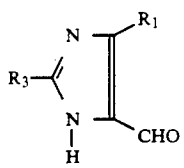

is coupled with a compound of the formula

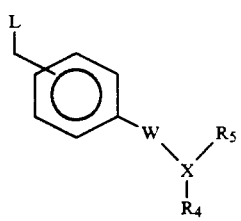

wherein L is a leaving group such as a halogen, in the presence of a coupling agent, e.g., potassium hexamethyldisilazane, in solvents such as tetrahydrofuran and dimethylformamide, to provide the compound

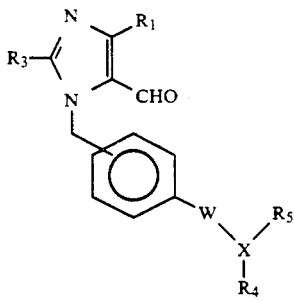

Aldehyde IV can thereafter be treated with a reducing agent, such as sodium borohydride, in a solvent such as ethanol to provide

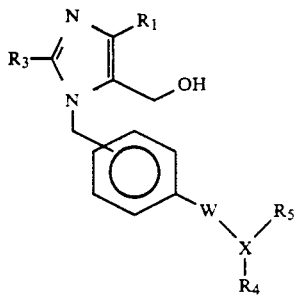

that is, compounds of formula I wherein $R_2$ is —CH$_2$—OH. Using known techniques, compounds of formula I where $R_2$ is other than —CH$_2$OH can be prepared from compound Ia. For example, alcohols of formula Ia can be alkylated or acylated to provide the corresponding products of formula I. Alternatively, compounds of formula I can be prepared from IV by Wittig homologation of the aldehyde.

The imidazole aldehyde II can be prepared by treating a compound of the formula

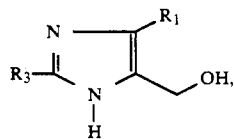

in pyridine, with an oxidizing agent, e.g., manganese oxide.

Compounds of formula III where X is $CR_4'$ and W=O, S or NH can be prepared by first reacting a compound of the formula

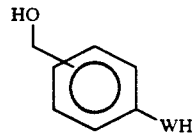

with a compound of the formula

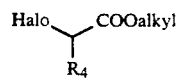

in a solvent, e.g., acetone, and in the presence of a base, e.g., potassium carbonate, to provide

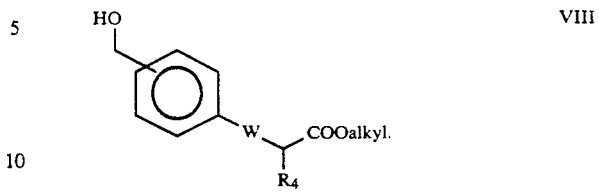

Intermediate VIII is thereafter treated to add a leaving group, e.g., a halogen group, which can be accomplished by known techniques. For example, treatment with thionyl chloride in a solvent, e.g., methylene chloride, provides

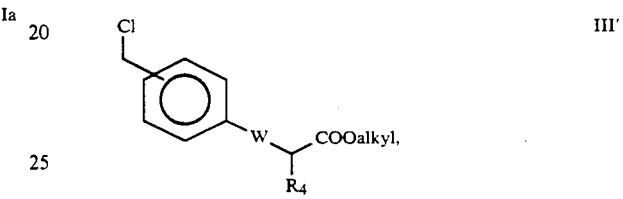

i.e., an intermediate of formula III wherein X is $CR_4'$, $R_5$ is —COOR$_7$ and $R_7$ is alkyl. Intermediate III' can be coupled to compound II, and thereafter treated as above to provide the corresponding products of formula I.

Compounds of formula I where X is $CR_4'$ and $R_5$ is other than —COOR$_7$ can be prepared from the compounds above using standard methodologies. For example, compounds where $R_5$ is one of the N-containing heterocyclic rings can be obtained by first treating an intermediate of formula VIII with methylchloroaluminum amide in a solvent, e.g., toluene, to provide

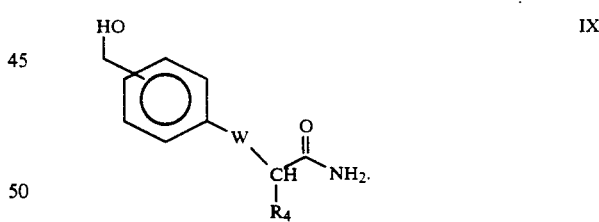

Intermediate IX in a mixture of solvents, e.g., pyridine and dioxane, can be treated with an anhydride, e.g., trifluoroacetic anhydride, to provide compounds of the formula

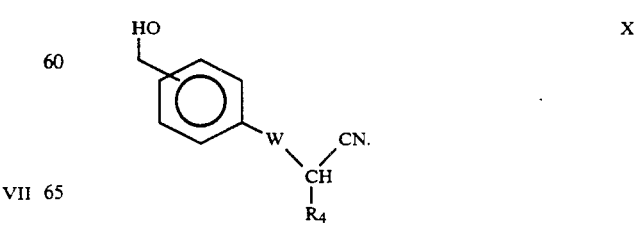

Treatment as with compound VIII above provides

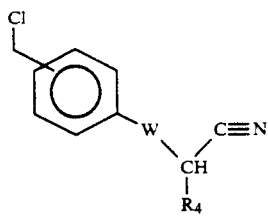

which can be coupled to compound II to provide

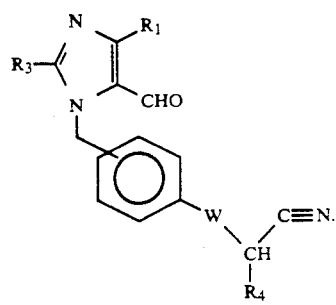

The aldehyde of formula XII is treated as IV above to provide the corresponding intermediates where $R_2$ is —$CH_2OH$, i.e.,

XIII

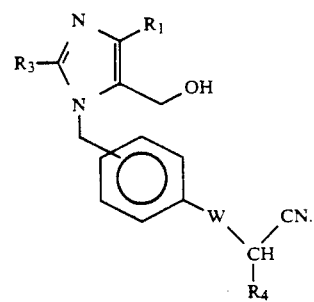

Thereafter, treatment of formula XIII with, for example, tri-n-butyl tin azide in a solvent, e.g., toluene, provides the tetrazole Ib

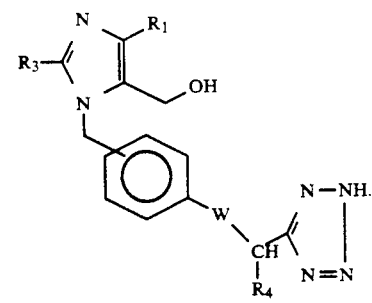

Intermediates XII and XIII can be converted to corresponding products where $R_2$ is other than —$CH_2OH$ using known methodologies as discussed above.

Products of formula I having other values for $R_5$ can be prepared by known methodology and starting with the appropriate intermediate of formula VIII.

Compounds of formula I wherein $R_1$ and $R_2$ together with the imidazole nucleus to which they are attached form a benzimidazole ring can be prepared using the methodology in U.S. Pat. No. 4,880,804.

To prepare the compound of formula I where W is $CH_2$ and X is N, a compound of the formula

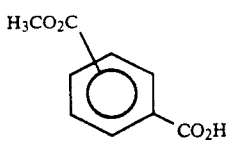

XIV is coupled with a compound of the formula $R_4NH_2$   XV in the presence of a coupling agent, e.g., dicyclohexylcarbodiimide to provide an amide of the formula

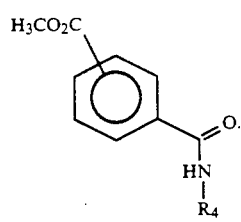

XVI

This can be reduced to the amine, for example with lithium aluminum hydride to provide

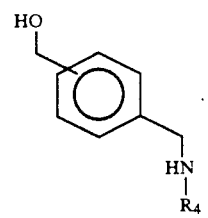

XVII

Intermediate XVII can thereafter be treated with formic acid in the presence of heat to provide a compound of the formula

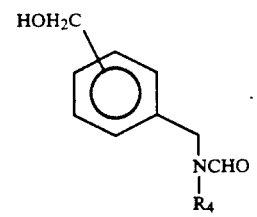

XIX

Treatment of compound XIX with an oxygen protecting group, "Prot", e.g., t-butyl diphenyl silyl, in the presence of an organic base, e.g., triethylamine and dimethylaminopyridine in a solvent, e.g., dichloromethane, provides compounds of the formula

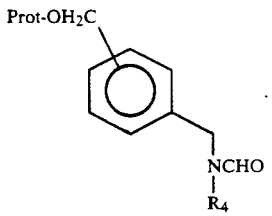

XX

Treatment of compound XX in a solvent, e.g., dichloromethane, with a dehydrating agent, e.g., oxalyl chloride, followed by treatment with tetrabutylammonium azide in the presence of an organic base, e.g., triethylamine, provides

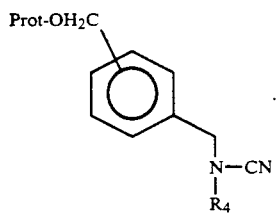

XXI

Deprotection of compound XXI, for example with tetrabutylammonium fluoride in a solvent such as tetrahydrofuran, provides compounds of the formula

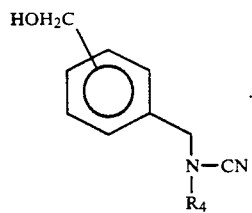

XXII

Treatment of compound XXII with triphenylphosphine in carbon tetrachloride provides

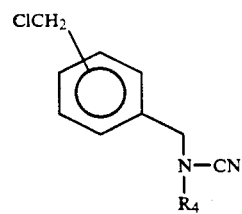

XXIII which can thereafter be coupled with a compound of formula II as descried above to provide

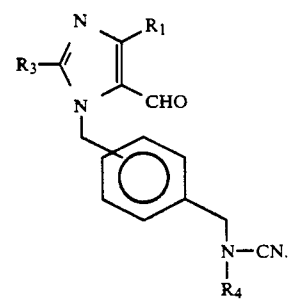

XXIV

Intermediates of formula XXIV can be treated with a reducing agent, e.g., sodium borohydride, to provide

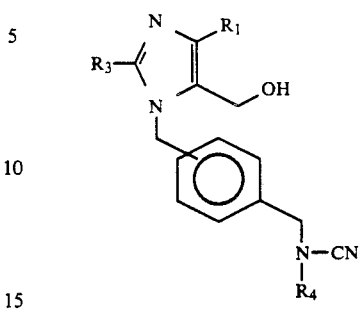

XXV which is treated with, for example, tri-n-butyl tin azide, to provide

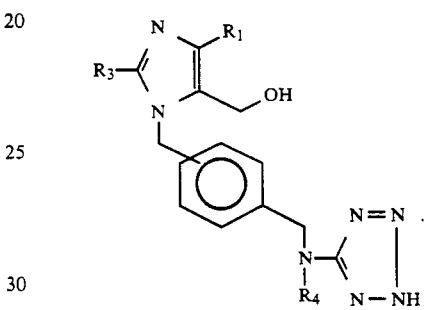

Ic

Intermediates XXIV and XXV can be converted to corresponding products where $R_2$ is other than —CH$_2$OH using known methodologies as discussed above.

Products of formula I having other values for $R_5$ can be prepared using known methodology starting with intermediate XIX.

Preferred compounds of the present invention are those wherein
W is O, S, NH;
X is $CR_4'$;
$R_1$ is hydrogen or halogen;
$R_2$ is —$(CH_2)_nOR_6$;
$R_3$ is $C_{2-10}$alkyl or $C_{3-10}$alkenyl;
$R_4$ is phenyl;
$R_4'$ is hydrogen; and
$R_5$ is —$COOR_7$ or tetrazolyl.

Most preferred compounds of the present invention are those wherein
W is O;
X is $CR_4'$;
$R_2$ is $CH_2OH$;
$R_3$ is $CH_2CH_2CH_2CH_3$;
$R_4$ is phenyl;
$R_4'$ is H; and,
$R_5$ is $CO_2H$.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive hear failure and cardiac hypertrophy.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

EXAMPLE 1

α-[4-[[2-Butyl-4-chloro-5-(hydroxymethyl)-1H-imidazol-1-yl ]methyl]phenoxy]benzeneacetic acid, monolithium salt A. α-[4-(Hydroxymethyl)phenoxy]benzeneacetic acid, methyl ester 4-Hydroxybenzyl alcohol (1.01 g, 8.12 mmol, 1.0 eq.) was combined with potassium carbonate (1.234 g, 8.93 mmol, 1.1 eq.) and 18-crown-6 (321.9 mg, 1.22 mmol, 0.15 eq.) in acetone (40.6 ml, 0.2M) and the mixture was heated at reflux for 1 hour. Methyl-alpha-bromophenyl acetate (1.28 ml, 8.12 mmol, 1.0 eq.) was then added and the reaction was heated at reflux for 4 hours. The mixture was then cooled to room temperature, filtered and concentrated. The residue was chromatographed on silica gel (100 g) eluting with ethyl acetate:toluene (1:8) followed by (1:7) to give 1.882 g of the title A compound.

B. α-[4-(Chloromethyl)phenoxy]benzeneacetic acid, methyl ester

The title A compound (598.6 mg, 2.20 mmol, 1.0 eq.) was dissolved in methylene chloride (2.2 ml, 1M) and treated at room temperature with thionyl chloride (1.21 ml of a 2M solution in methylene chloride, 2.42 mmol, 1.1 eq.). The reaction was stirred at room temperature for 30 minutes and concentrated. The residue was chromatographed on silica gel (20 g) eluting with chloroform:hexane (3:2) to give 557.5 mg of the title B product.

C. Pentanamidic acid, ethyl ester hydrochloride

Hydrogen chloride gas was bubbled into a tared solution of valeronitrile (92.0 g, 1.08 mole) in absolute ethanol (64 ml, 1.08 mole) in a 1-liter round bottomed flask cooled to 0° C. The flask was weighed periodically and hydrogen chloride bubbling was continued until the weight gain was greater than 39 g (1.08 mole). The mixture was then stoppered and stored at 0° C. for 6 days. Ether (650 ml) was then added (cold) and the mixture was stored at −30° C. for 24 hours. The resulting solid was collected on a buchner funnel, transferred quickly to a large beaker, triturated quickly with cold ether, and collected again on a buchner funnel. The solid was then dried in vacuum to give the title C compound as a free flowing white solid (95 g).

D. 2-Butyl-4-(hydroxymethyl)-imidazole

A 300 ml stainless steel Parr pressure bomb containing dihydroxyactone dimer (5.0 g, 55 mmol) was cooled in a dry ice bath for one hour. During the cooling period, the bomb lid was set on top of the bomb and held in place by applying a light vacuum; the associated hardware for holding the lid in place under pressure was not cooled (to facilitate handling later). When the bomb was sufficiently cooled, liquid ammonia was condensed into a 250 ml three neck flask fitted with a dry ice condenser at −78° C. The cold bomb was then opened by releasing the vacuum, the title C compound (9.1 g, 55 mmol) was added, followed immediately by liquid ammonia from the 250 ml flask (approx. 55 ml of ammonia were added). The bomb was sealed using the appropriate hardware, removed from the dry ice bath, and allowed to warm to room temperature. The bomb was then immersed about half way in an oil bath and heated to 75° C. for three hours, during which the pressure rose to 320 psi. Heating was then discontinued and the bomb was allowed to cool to room temperature. When the pressure dropped below 100 psi, the pressure relief valve was slowly opened and the ammonia was allowed to evaporate (evaporative cooling helped cool the bomb). When the pressure was completely equilibrated, the bomb was opened and its contents were transferred to a conventional flask using acetonitrile to wash the residue out. The mixture was concentrated in vacuo and the residue was purified by flash chromatography on silica gel (1500 g), eluting with 80:20:1 chloroform:methanol:ammonium hydroxide. Fractions containing the major product ($R_f$ 0.5) were combined and concentrated. The residue was then crystallized from acetonitrile (200 ml) to give a white crystalline solid (5.74 g), m.p. 92°–93° C., which is 2-butyl-4-(hydroxymethyl)imidazole, i.e., the title D compound.

E. 2-Butyl-4-chloro-5-formyl imidazole

A solution of the title D compound (6.15 g, 39.9 mmol) in a mixture of absolute ethanol (40 ml) and tetrahydrofuran (80 ml) was cooled in an ice bath. To the cold solution was added N-chlorosuccinimide (5.9 g, 44.4 mmol) in small portions over 60 minutes. The resulting mixture was stirred for 30 minutes in the ice bath, then for 30 minutes at 25° C., after which a starch-iodine test was negative. The mixture was concentrated in vacuo to give a residue which was triturated with ether (400 ml) to give a tan solid. The mother liquor from trituration was concentrated and the residue was re-triturated with ether (40 ml) to give more of the tan solid. The solids were combined, dissolved in pyridine (200 ml), and warmed to 100° C. Manganese dioxide (20 g) was added to the warm solution and the resulting black mixture was stirred at 100° C. for one hour. The hot solution was filtered and concentrated. The residue was purified by chromatography on silica gel (500 g), eluting with 3:1 hexane:ethyl acetate, to give a major product having $R_f$ 0.4. The product was triturated with petroleum ether to give the title E compound as a white crystalline solid (3.9), m.p. 96°–97° C.

F. α-[4-[[2-Butyl-4-chloro-5-formyl-1-imidazol-1-yl]methyl]phenoxy]benzeneacetic acid, methyl ester The title B compound (209.6 mg, 0.721 mmol, 1.0 eq.) was combined with the title E compound (148 mg, 0.793 mmol, 1.1 eq.) and dissolved in dimethylformamide (3.6 ml, 0.2M). The solution was then treated with potassium t-butoxide (106 mg, 0.901 mmol, 1.25 eq.) and 18-crown-6 (38.1 mg, 0.144 mmol, 0.2 eq.) and stirred at room temperature overnight. The mixture was quenched with aqueous saturated ammonium chloride and water, and extracted three times with ethyl acetate. The organic extracts were dried over sodium sulfate, filtered through magnesium sulfate and concentrated. The residue was chromatographed on silica gel (18 g) eluting with toluene:ether (16:1) to give the title F compound (228 mg).

G. α-[4-[[2-Butyl-4-chloro-5-(hydroxymethyl)-1H-imidazol-1-yl]methyl]phenoxy]benzene-acetic acid, ethyl ester The title F compound (228 mg, 0.518 mmol, 1.0 eq.) was dissolved in ethanol (5.2 ml, 0.1M) and treated at room temperature with sodium borohydride (19.6 mg, 0.518 mmol, 1.0 eq.) dissolved in ethanol (1.96 ml). After 40 minutes at room temperature, the reaction was quenched with 1N hydrogen chloride and concentrated. Saturated aqueous sodium hydrogen carbonate was added to the residue and the aqueous mixture was extracted three times with ethyl acetate. The organic extracts were dried over sodium sulfate, filtered through magnesium sulfate and concentrated. The residue was chromatographed on silica gel (10 g) eluting with hexane:acetone: ammonium hydroxide (40:10:0.05) followed by (30:10: 0.05) to give the title G compound (170 mg).

H. α-[4-[[2-Butyl-4-chloro-5-(hydroxymethyl)-1H-imidazol-1-yl]methyl]phenoxy]benzene-acetic acid, monolithium salt The title G compound (170 mg, 0.373 mmol, 1.0 eq.) was dissolved in methanol (2 ml) and aqueous 1N lithium hydroxide (2 ml). The reaction was stirred at room temperature for 3 hours and concentrated. The residue was chromatographed on HP-20 resin (10 g) eluting with water (70 ml), 2% acetone in water (70 ml), 5% acetone in water (70 ml), 10% acetone in water (70 ml), and 20% acetone in water (70 ml). The product eluted between 5% and 20%. The fractions were concentrated to a volume of ~20 ml and lyophilized. The product was thereafter dissolved in water (15 ml), filtered through a polycarbonate membrane and lyophilized to give 141 mg of the title compound, m.p. >250° C. $R_f$=0.26, silica gel, chloroform:methanol:acetic acid (30:4:0.5), cobalt stain.

Analysis calc'd for $C_{23}H_{24}ClN_2O_4 \cdot Li \cdot 1.1\, H_2O$:
C, 60.76; H, 5.81; N, 6.16; Cl, 7.80;
Found: C, 60.72; H, 5.72; N, 6.08; Cl, 7.93.

EXAMPLE 2

2-Butyl-4-chloro-1-[4-[phenyl(2H-tetrazol-5-yl)methoxy]phenyl]methyl]-1H-imidazole-5-methanol

A. α-[4-(Hydroxymethyl)phenoxy]benzene-acetamide

The title A compound from Example 1 (10.84 g, 0.398 mol) was dissolved in 25 ml toluene and was added via addition funnel to a stirring solution of methyl chloroaluminum amide (0.507 mol) (0.67 m in toluene) (prepared according to Weinreb, *Synthetic Communications*, 12(13), 989 (1982)). Upon full addition, reaction was heated to 50° C. for 7 hours. Reaction was then cooled to ≦10° C. in a water/ice bath and the entire reaction was slowly quenched by adding ~100 ml of 1.0N hydrogen chloride slowly enough to keep temperature ≦15° C. and keeping bubbling to a minimum. Reaction was then extracted four times with ethyl acetate, combined organics were dried and concentrated. The product was flash chromatographed in 60:40 hexane:acetone followed by 50:50. The product was isolated and concentrated to yield 8.51 g of the title A compound.

B. α-4-(Hydroxymethyl)phenoxy]benzene-acetonitrile

The title A compound (8.43 g, 0.0328 mol) was dissolved in 1,4 dioxane (325 ml, 0.1M) and 0.1148 mol of pyridine was added at room temperature. This solution was cooled to ≦10° C. in an ice-water bath, then trifluoroacetic anhydride (0.082 mol) was slowly added via syringe to the cooled reaction. Reaction was then allowed to warm to room temperature. The reaction was then concentrated, diluted in ethyl ether and washed with 1N hydrogen chloride. The aqueous portion was re-extracted with ethyl ether, then combined organics were washed with saturated sodium hydrogen carbonate, dried and concentrated. This crude reaction mixture was stirred at room temperature in methanol for 2.5 hours, then the solution was concentrated and flash chromatographed on silica gel in 60:40 hexane:ethyl acetate. Product was isolated to provide 6.08 g of the title B compound.

C. α-[4-(Chloromethyl)phenoxy]benzene-acetonitrile

The title B compound (6.03 g, 0.0252 mol) was dissolved in approximately 50 ml (0.5M) of methylene chloride then 15.0 ml of a 2.0M solution of thionyl chloride in methylene chloride was slowly added via syringe to the reaction. The reaction was stirred at room temperature for 1.75 hours. The reaction was then concentrated and flash chromatographed in 1:1 $CHCl_3$:hexane to provide 5.49 g of the title C compound.

D.
α-[4-[[2-Butyl-4-chloro-5-formyl-1H-imidaxol-1-yl]methyl]phenoxy]benzene-acetonitrile The title C compound (1.5 g, 5.82 mmol) and the title E compound of Example 1 (1.195 g, 6.40 mmol) were dissolved in 30 ml dimethylformamide (approx. 2M) and 18-crown-6 (0.308 g, 1.16 mmol) was added. The reaction was then cooled to $\leq 10°$ C. in an ice water bath, then potassium-t-butoxide (0.816 g, 7.26 mmol) was added. Upon full addition, reaction was heated to 40° C. for 12 hours overnight. Water was then added to the reaction, and then this was extracted three times with ethyl acetate. The combined organics were dried, concentrated and flash chromatographed on silica gel eluting with 95:5 toluene:ethyl ether to provide 1.73 g of the title D compound.

E.
α[4-[[2-Butyl-4-chloro-5-(hydroxymethyl)-1H-imidazol-1-yl]methyl]phenoxy]benzene-acetonitrile The title D compound (1.73 g, 4.24 mmol) dissolved in 45 ml ethanol cooled to $\leq 10°$ C. Sodium borohydride (0.16 g, 4.24 mmol) in 16 ml of absolute ethanol was slowly added to the reaction. Upon full addition, the reaction was allowed to reach room temperature. The pH was then adjusted to pH ~4 by the dropwise addition of 1N hydrogen chloride. The reaction was then concentrated, diluted in ethyl acetate, washed with saturated sodium hydrogen carbonate and water, and flash chromatographed on silica gel in 70:30 $CHCl_3:Et_2O$ to give the title E compound (1.37 g).

F.
2-Butyl-4-chloro-[[4-[phenyl(2H-tetrazol-5-yl)methoxy]phenyl]methyl]-1H-imidazolep-5-methanol The title E compound (1.27 g, 3.098 mmol) was dissolved in 6 ml toluene (0.5M) and then tri-n-butyl tin azide (4.63 g, 13.94 mmol) was added at room temperature. The reaction was then heated to 100° C. for 5.5 hours. The solution was concentrated and dissolved in a 90:10 $CH_2Cl_2$: MeOH mixture. The organic phase was extracted three times with a 1.0M lithium hydroxide solution and the aqueous phase was lyophilized. The crude product was passed through a column of HP-20 resin eluting with 100% water to 50:50 water/acetone in 5% increments, and thereafter rechromatographed eluting with 100% water to 80:20 water/acetone in 5% intervals to provide 0.309 g of the title product, m.p. 208°-250° C. (dec). TLC: ($SiO_2$; 25:8:0.05, $CHCl_3$: MeOH:HOAc) $R_f$ 0.29 (uv).

Analysis calc'd for $C_{23}H_{24}ClN_6O_2 \cdot Li \cdot 1.25\ H_2O$:
C, 57.38; H, 5.55; N, 17.46; Cl, 7.36;
Found: C, 57.28; H, 5.48; N, 17.42; Cl, 7.53.

What is claimed is:
1. A compound of the formula

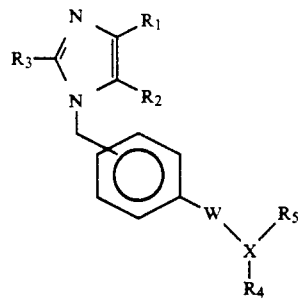

or a pharmaceutically acceptable salt thereof, where
$R_1$ is H, halogen, $NO_2$, $CF_3$, CN;
$R_2$ is H, —CN, $C_{1-10}$alkyl, $C_{2-10}$alkenyl or the same groups optionally substituted with fluoro, and phenyl $C_{1-6}$alkenyl;
$R_3$ is alkyl of 2 to 10 carbon atoms, alkenyl or alkynyl of 3 to 10 carbon atoms or the same groups substituted with F or $CO_2R_7$; cycloalkyl of 3 to 8 carbon atoms, cycloalkylalkyl of 4 to 10 carbon atoms; cycloalkylalkenyl or cycloalkylalkynyl or 5 to 10 carbon atoms; $(CH_2)_sZ(CH_2)_mR'$ (wherein R' is H, $C_{1-6}$alkyl, $C_{3-6}$cycloalkyl, $C_{2-4}$alkenyl or $C_{2-4}$alkynyl) optionally substituted with F or $CO_2R_7$; benzyl or benzyl substituted on the phenyl ring with 1 or 2 halogens, alkoxy of 1 to 4 carbon atoms, alkyl of 1 to 4 carbon atoms or nitro;
W is —O—;
X is —$CR_4$';
$R_4$ and $R_4'$ are each independently hydrogen, alkyl of 1 to 10 carbon atoms, alkenyl or alkynyl of 3 to 10 carbon atoms, cycloakyl of 3 to 8 carbon atoms, cycloalkylalkyl of 4 to 10 carbon atoms, cycloalkylalkenyl or cycloalkylalkynyl of 5 to 10 carbon atoms, aryl of aryl substituted with any $R_5$ group, benzyl or benzyl substituted on the phenyl ring with 1 or 2 halogens, alkoxy of 1 to 4 carbon atoms, alkyl of 1 to 4 carbon atoms, nitro; and,
$R_5$ is —COOH or tetrazolyl.
2. A compound of claim 1 having the name α-[4-[[2-butyl-4-chloro-5-(hydroxymethyl)-1H-imidazol-1-yl]methyl]phenoxy]benzeneacetic acid, monolithium salt.
3. A compound of claim 1 having the name 2-Butyl-4-chloro-1[[4-[phenyl(2H-tetrazol-5-yl)-methoxy]-phenyl]methyl]-1H-imidazole-5-methanol.

* * * * *